United States Patent
Yamazaki et al.

(10) Patent No.: US 6,627,187 B2
(45) Date of Patent: *Sep. 30, 2003

(54) ERYTHROPOIETIN SOLUTION PREPARATION

(75) Inventors: Tadao Yamazaki, Tokyo (JP); Toshiari Morita, Tokyo (JP); Hiroshi Nagai, Tokyo (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 162 days.

This patent is subject to a terminal disclaimer.

(21) Appl. No.: 09/909,429

(22) Filed: Jul. 18, 2001

(65) Prior Publication Data

US 2001/0055582 A1 Dec. 27, 2001

Related U.S. Application Data

(63) Continuation of application No. 09/468,772, filed on Dec. 21, 1999, now Pat. No. 6,277,367, which is a continuation of application No. 09/171,737, filed as application No. PCT/JP97/01449 on Apr. 25, 1997, now Pat. No. 6,120,761.

(30) Foreign Application Priority Data

Apr. 26, 1996 (JP) .............................................. 8-131226
Oct. 30, 1996 (JP) .............................................. 8-303956

(51) Int. Cl.$^7$ ......................... A61K 38/19; A61K 38/22
(52) U.S. Cl. ........................................ 424/85.1; 514/21
(58) Field of Search ................................. 530/350, 351, 530/397; 514/8, 12, 21; 424/85.1

(56) References Cited

U.S. PATENT DOCUMENTS

| | | | |
|---|---|---|---|
| 4,877,608 A | 10/1989 | Lee et al. | 424/85.8 |
| 4,992,419 A | 2/1991 | Woog et al. | 514/8 |
| 5,580,856 A | 12/1996 | Prestrelski et al. | 514/21 |
| 5,691,312 A | 11/1997 | Paques | 514/12 |
| 6,120,761 A * | 9/2000 | Yamazaki et al. | 424/85.1 |
| 6,277,367 B1 * | 8/2001 | Yamazaki et al. | 424/85.1 |

FOREIGN PATENT DOCUMENTS

| | | |
|---|---|---|
| JP | 61-97229 | 5/1986 |
| JP | 62-123130 | 6/1987 |
| JP | 63-146829 | 6/1988 |
| JP | 64-42442 | 2/1989 |
| JP | 64-71818 | 3/1989 |
| JP | 03-044333 | 2/1991 |
| JP | 3-170437 | 7/1991 |
| JP | 4-108737 | 4/1992 |
| WO | 93/03744 | 3/1993 |
| WO | 96/17593 | 6/1996 |
| WO | 96/28143 | 9/1996 |

* cited by examiner

Primary Examiner—Jeffrey E. Russel
(74) Attorney, Agent, or Firm—Morgan & Finnegan, LLP

(57) ABSTRACT

This invention provides an erythropoietin solution preparation containing an amino acid as a stabilizer, and having excellent long-term storage stability.

19 Claims, 4 Drawing Sheets

1 2 3 4 5 6 7 8 9 10

ERYTHROPOIETIN SOLUTION PREPARATION

This is a continuation application of U.S. Ser. No. 09/468,772 filed Dec. 21, 1999, now U.S. Pat. No. 6,277,367, which is a continuation of U.S. Ser. No. 09/171,737 filed Dec. 16, 1998, which issued U.S. Pat. No. 6,120,761, which is a 35 U.S.C. 371 filing of PCT/JP 97/01449 filed Apr. 25, 1997.

TECHNICAL FIELD

This invention relates to an erythropoietin solution preparation.

BACKGROUND ART

Erythropoietin (hereinafter referred to as EPO) is an acidic glycoprotein hormone which promotes the differentiation and proliferation of erythroid progenitor cells. This hormone is secreted chiefly by the kidney. Erythrocytes are present abundantly in the blood for certain periods, and are then destroyed by the spleen, etc. (their mean life in humans is about 120 days). However, red blood cells are constantly supplied from the bone marrow, so that the peripheral total erythrocyte count is kept constant in a normal state. EPO plays a central role in maintaining such homeostasis of erythrocytes in the living organism.

High purity human urinary EPO was obtained by purification from a large volume of urine from patients with aplastic anemia. This enabled cloning of human EPO gene. Nowadays, it has become possible to produce a large amount of recombinant human EPO in animal cells by genetic engineering technology. The applicant of this invention has succeeded in producing a preparation (lyophilized preparation) of the purified EPO, and supplies it to the market in the form of renal anemia alleviating agents and so on.

Drug design for supplying the market with stable EPO preparations requires that chemical changes (hydrolysis, disulfide exchange reaction, etc.) or physical changes (denaturation, agglutination, adsorption, etc.) observed with EPO be suppressed. Products now on the market contain human serum albumin or purified gelatin which is generally used as a stabilizer. These substances have been added in these products to suppress chemical or physical changes. Since human serum albumin is a blood product relying on donated blood for its supply, the necessity for its addition has been questioned. Regarding the addition of a protein other than the albumin or gelatin as a stabilizer, it is difficult to avoid the risk of viral contamination completely.

Peptide drugs are often lyophilized for stabilization. However, lyophilization increases manufacturing costs, and involves an increased risk due to mechanical troubles.

For the foregoing reasons, demand is growing for an EPO preparation as an alternative to a lyophilized preparation, the EPO preparation being free from inclusion of a protein as a stabilizer, and stable during long-term storage.

DISCLOSURE OF THE INVENTION

To satisfy the above demand, we, the inventors, have conducted extensive studies. As a result, we have found that EPO can be converted into a stable EPO solution preparation free from human serum albumin and purified gelatin by adding a certain amino acid as a stabilizer. This finding has led us to complete the present invention.

That is, the present invention provides an erythropoietin solution preparation containing an amino acid as a stabilizing agent or stabilizer.

"To stabilize; stabilizing" in this specification refers to storing, or the erythropoietin solution preparation, for example, for more than 2 years at 10° C., or for more than 6 months at 25° C., or for more than 2 weeks at 40° C. while keeping the residual rate of erythropoietin at 90% or higher, preferably 95% or higher, more preferably 98% or higher.

BEST MODE FOR CARRYING OUT THE INVENTION

Figure 1:
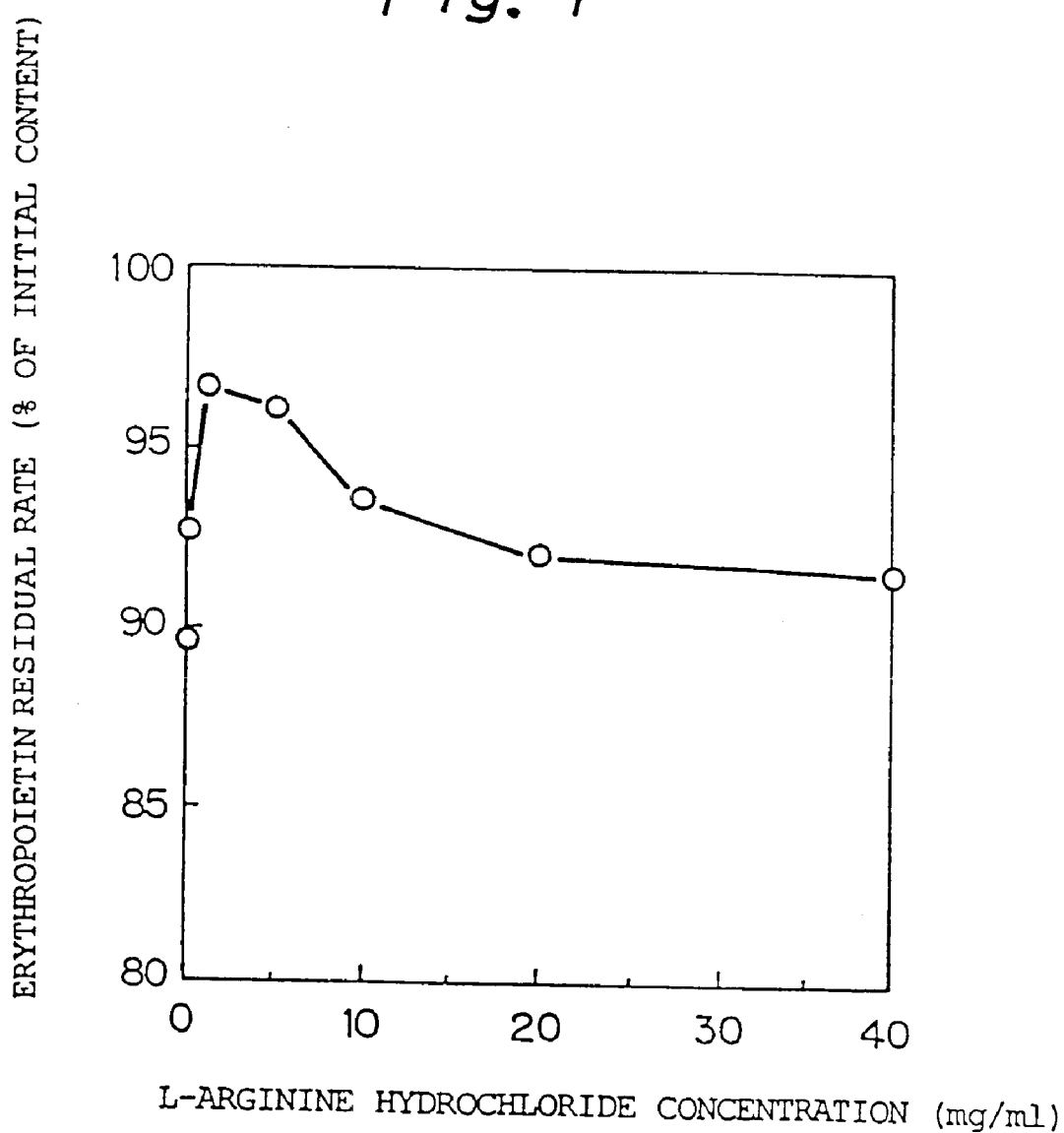
FIG. 1 is a graph showing the relation between the concentration of L-arginine hydrochloride and the residual rate of erythropoietin.

EPO for use in the solution preparation of the present invention has substantially the same biological activity as that of mammalian, especially, human EPO, and includes naturally occurring EPO and EPO obtained by genetic recombination. EPO from genetic recombination includes EPO having the same amino acid sequence as that of naturally occurring EPO, or EPO with this amino acid sequence from which one or more of the amino acids have been deleted, or in which one or more of the amino acids have been substituted, or to which one or more amino acids have been added, and which, however, retains the above-mentioned biological activity. The EPO in the present invention may be produced by any methods, for example, a method comprising extraction from human urine, followed by separation and purification, in various manners; and a method involving production in E. coli, yeast, or Chinese hamster ovary cells, followed by extraction, separation and purification in various manners.

The amino acid added as a stabilizer in the present invention includes free amino acids, and their salts such as sodium salts, potassium salts and hydrochlorides. The solution preparation of the present invention may have one or more of these amino acids added in combination. The preferred amino acids are D-, L- and DL-forms of leucine, tryptophan, serine, glutamic acid, arginine, histidine and lysine, and their salts. More preferable are L-leucine, L-tryptophan, L-glutamic acid, L-arginine, L-histidine and L-lysine, and their salts. Particularly preferable are L-arginine, L-histidine and L-lysine, and their salts. Most preferable are L-histidine and its salts.

The solution preparation of the present invention, preferably, is substantially free from protein as a stabilizer.

For the amount of the amino acid added to the solution preparation of the present invention, a preferred range can be set by a testing method (to be described later on) depending on the type of the amino acid used. Generally, the amount of the amino acid added is 0.001 to 50 mg/ml, but preferably 0.1 to 40 mg/ml, more preferably 1 to 10 mg/ml for arginine, preferably 0.5 to 10 mg/ml, more preferably 1 to 10 mg/ml for lysine, preferably 0.5 to 10 mg/ml, more preferably 1.0 to 4.0 mg/ml, and most preferably 1.0 to 2.0 mg/ml for histidine. As will be described later on, the highest residual rate of EPO was obtained when L-arginine hydrochloride and L-lysine hydrochloride were each added in an amount of about 1 to 5 mg/ml as free amino acid, or when L-histidine hydrochloride was added in an amount, as free amino acid, of 1 to 10 mg/ml in an accelerated testing performed for 2 weeks at 40° C., or 0.5 to 5 mg/ml in a 25° C.-6 month accelerated testing.

The amount of EPO contained in the solution preparation of the present invention can be determined according to the type of disease to be treated, the severity of the disease, the age of the patient, and so forth. Generally, its amount is 100 to 500,000 IU/ml, preferably 200 to 100,000 IU/ml, more preferably 750 to 72,000 IU/mi. The solution preparation of the present invention is administered usually by a parenteral route, for example, by injection (subcutaneous or intravenous), or percutaneously, transmucosally or transnasally, but oral administration is also possible.

The solution preparation of the present invention may contain, in addition to EPO and the amino acid, ingredients usually added to a preparation in the form of a solution, such as polyethylene glycol; sugars, e.g., dextran, mannitol, sorbitol, inositol, glucose, fructose, lactose, xylose, mannose, maltose, sucrose, and raffinose; inorganic salts, e.g., sodium chloride, potassium chloride, calcium chloride, sodium phosphate, potassium phosphate, and sodium hydrogen carbonate; organic salts, e.g., sodium citrate, potassium citrate and sodium acetate; and, if desired, sulfur-containing reducing agents, e.g., glutathione, thioctic acid, sodium thioglycolate, thioglycerol, α-monothioglycerol, and sodium thiosulfate. The preferred salt is sodium chloride. It is also preferred to add an adsorption preventing agent, such as a polyoxyethylene sorbitan alkyl ester, to the solution preparation of the present invention. Particularly preferable polyoxyethylene sorbitan alkyl esters are polysorbate 20, 21, 40, 60, 65, 80, 81 and 85, and most preferably, polysorbate 20 and/or 80. The preferred amount of polysorbate 20 and/or 80 added is 0.01 to 1 mg/ml, more preferably 0.05 to 0.1 mg/ml.

The solution preparation of the present invention can be prepared by dissolving the above-mentioned components in an aqueous buffer publicly known in the field of solution preparations, such as phosphate and/or citrate buffer. The preferred phosphate buffer is a sodium monohydrogen phosphate-sodium dihydrogen phosphate buffer, while the preferred citrate buffer is a sodium citrate buffer. The pH of the solution preparation of the present invention is 5.0 to 8.0, preferably, 6.0 to 7.0.

Japanese Unexamined Patent Publication No. 64-71818 discloses a human protein preparation characterized by containing urea, an amino acid, and a nonionic wetting agent. However, the solution preparation of the present invention preferably does not contain urea, because it is not clear whether urea contributes to the long-term stabilization of a glycoprotein such as erythropoietin. A reaction between urea degradation products and protein is also known to take place (Protein Chemistry 3, Kyoritsu Shuppan, Chapter 12), which may adversely affect the preparation. Furthermore, the fewer ingredients added to the preparation, the better the results that can be expected.

The solution preparation of the present invention is usually contained in a sealed, sterilized plastic or glass container. The solution preparation can be supplied as a prescribed dose in an ampoule, vial or disposable syringe, or in a multiple dose form such as a bag or bottle for injection.

EPO solution preparations containing various amino acids were prepared, and subjected to an accelerated testing conducted for 2 weeks at 40° C. The EPO content in each of the preparations after the test was measured by RP-HPLC (reversed phase high performance liquid chromatography) to investigate the effect of amino acid addition on this content. As a result, the residual rate of EPO was found to be higher in the solution preparations containing L-leucine, L-tryptophan, monosodium L-glutamate monohydrate, L-arginine hydrochloride, L-histidine hydrochloride, and L-lysine hydrochloride than in the solution preparations containing no amino acids. The results of SDS-polyacrylamide gel electrophoresis demonstrated L-arginine hydrochloride and L-histidine hydrochloride to be effective in suppressing the formation of EPO degradation products to be observed in the preparation after the accelerated testing.

Of the amino acids thus shown to be effective when added, L-arginine hydrochloride, L-lysine hydrochloride and L-histidine hydrochloride were examined for the effect of their concentrations on the stabilization of the preparation. That is, EPO preparations to which L-arginine hydrochloride, L-lysine hydrochloride or L-histidine hydrochloride was added in various concentrations were made, and a 40° C.-2 week accelerated testing was conducted on these preparations. Upon completion of the test, the residual rates of EPO in the preparations tended to peak at concentrations of about 1 to 5 mg/ml in the case of L-arginine hydrochloride and L-lysine hydrochloride. With L-histidine hydrochloride, maximum EPO residual rate was achieved at a concentration of 1 to 10 mg/ml. A 25° C.-6 month accelerated testing was also performed in EPO preparations to which L-histidine hydrochloride was added in various concentrations. The EPO residual rate was maximal at the concentrations of 0.5 to 5 mg/ml. These findings showed L-arginine hydrochloride, L-lysine hydrochloride, and L-histidine hydrochloride to have the optimum concentration of addition.

The EPO solution preparation of the present invention is a safe preparation free from foreign proteins such as human serum albumin or purified gelatin, and without the risk of viral contamination. The amino acid added thereto is cheaper than these conventional stabilizers, and the cost incurred during the manufacturing process is also lower than that for a lyophilized product. Thus, the preparation of this invention is advantageous economically. Furthermore, the solution preparation of the present invention need not be dissolved in a buffer, but can be used as it is. This lessens labor in using it in comparison with a lyophilized preparation. Because of these various advantages, the industrial applicability of the present invention is great.

The present invention will now be described in further detail by reference to the following examples, but its scope is not restricted thereby.

EXAMPLES

Testing Method

A 5 ml glass vial was charged with 1 ml of a dispensing solution containing the following components/ml and being adjusted to pH 6.0 with a 10 mM phosphate buffer (Wako Pure Chemical Industries, Ltd.):

| | |
|---|---|
| EPO | 1,500 IU |
| Nonionic surfactant (polysorbate 80, Nikko Chemical Co., Ltd.) | 0.05 mg |
| Sodium chloride | 8.5 mg |
| Amino acid (Sigma Chemical Company) | 0 to 40 mg |

The filled vial was stoppered, sealed, and used as a solution preparation. As an accelerated testing, the preparation was allowed to stand for 2 weeks in a thermostatic chamber at 40° C. Then, the preparation was evaluated by RP-HPLC analysis (WATERS) and SDS-polyacrylamide gel electrophoresis analysis.

Example 1
Effect of the Addition of Various Amino Acids on EPO Residual Rate

In accordance with the foregoing testing method, the solution preparations containing various amino acids tabulated below were produced, and subjected to the 40° C.-2 week accelerated testing. Then, their EPO residual rates were determined by the RP-HPLC method. The results are shown in Table 1.

TABLE 1

EPO residual rates after accelerated testing of various amino acids-containing solution preparations

| Amino acid | Amount added (mg/ml) | EPO residual rate after 40° C.-2 week accelerated testing (% of initial content) |
|---|---|---|
| Not added | 0 | 83.9 |
| L-leucine | 10 | 91.6 |
| L-phenylalanine | 10 | 57.8 |
| L-tryptophan | 5 | 97.0 |
| L-serine | 10 | 85.2 |
| L-cysteine | 10 | 47.1 |
| Monosodium L-glutamate monohydrate | 10 | 93.9 |
| L-arginine hydrochloride | 10 | 93.6 |
| L-histidine hydrochloride | 10 | 99.7 |
| L-lysine hydrochloride | 10 | 95.8 |

As shown above, L-leucine, L-tryptophan, monosodium L-glutamate monohydrate, L-arginine hydrochloride, L-histidine hydrochloride, and L-lysine hydrochloride led to particularly marked EPO residual rates.

Example 2
Effect of the Addition of an Amino Acid in Various Concentrations on EPO Residual Rate In accordance with the foregoing testing method, EPO solution preparations containing L-arginine hydrochloride in various concentrations indicated below were produced, and subjected to the same 40° C.-2 week accelerated testing. Then, their EPO residual rates were determined by the RP-HPLC method. The results are shown in Table 2.

TABLE 2

EPO residual rates after accelerated testing of L-arginine hydrochloride-containing preparations

| Amino acid | Amount added (mg/ml) | EPO residual rate after 40° C.-2 week accelerated testing (% of initial content) |
|---|---|---|
| Not added | 0 | 89.6 |
| L-arginine hydrochloride | 0.1 | 92.7 |
| | 1 | 96.7 |
| | 5 | 96.1 |
| | 10 | 93.6 |
| | 20 | 92.0 |
| | 40 | 91.6 |

The above results are depicted as a graph in FIG. 1.

As shown above, L-arginine hydrochloride led to maximum EPO residual rates in a concentration range of about 1 to 5 mg/ml.

Then, the same test was conducted using L-lysine hydrochloride. The amounts of L-lysine hydrochloride added and the EPO residual rates after the accelerated testing are shown in Table 3.

TABLE 3

EPO residual rates after accelerated testing of L-lysine hydrochloride-containing preparations

| Amino acid | Amount added (mg/ml) | EPO residual rate after 40° C.-2 week accelerated testing (% of initial content) |
|---|---|---|
| Not added | 0 | 88.7 |
| L-lysine hydrochloride | 0.5 | 93.1 |
| | 1 | 95.8 |
| | 5 | 96.3 |
| | 10 | 90.2 |

Figure 2:
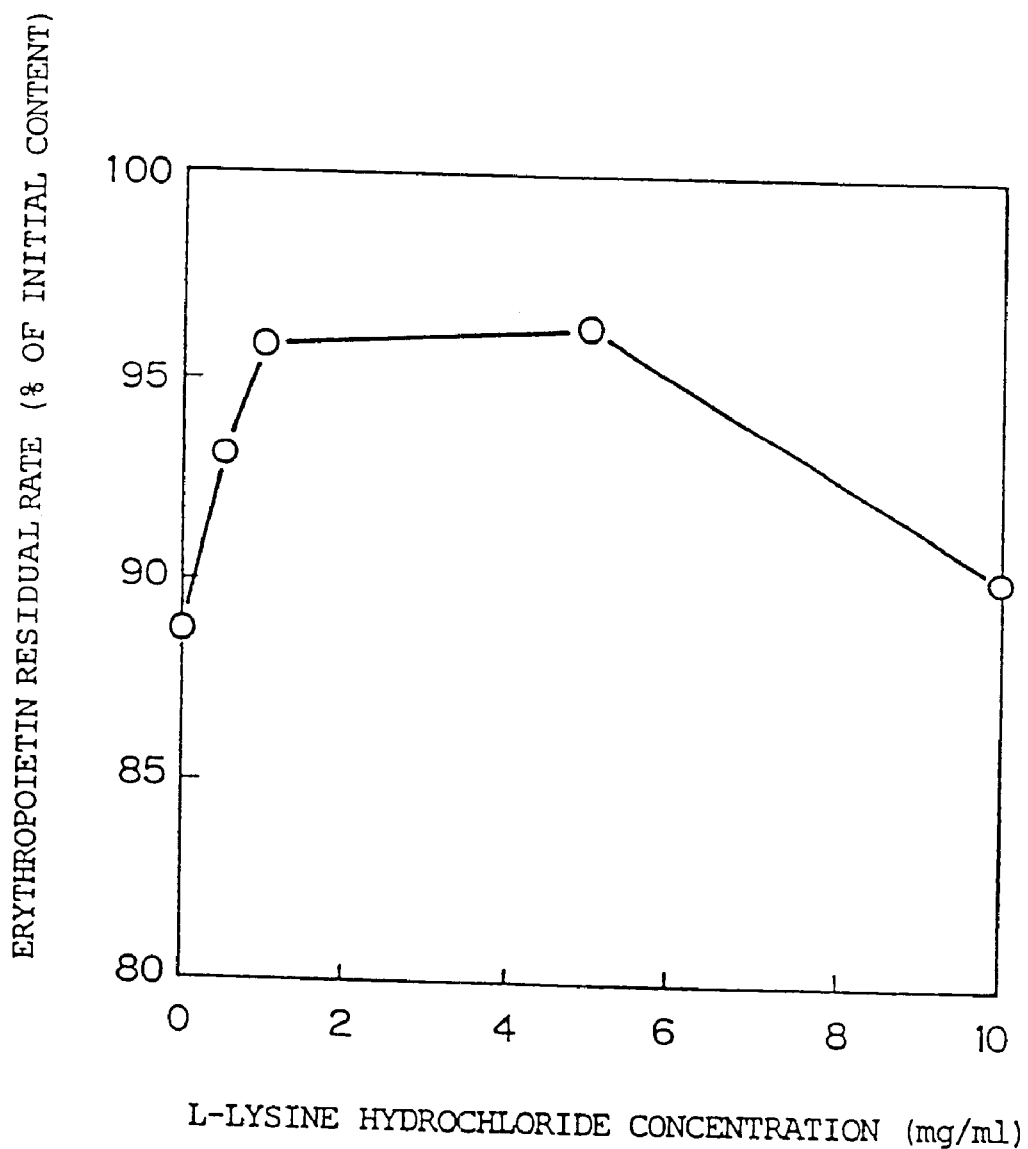
FIG. 2 is a graph showing the relation between the concentration of L-lysine hydrochloride and the residual rate of erythropoietin.

The above results are depicted as a graph in FIG. 2.

As shown above, L-lysine hydrochloride also led to maximum EPO residual rates in a concentration range of about 1 to 5 mg/ml.

Then, the same test was conducted using L-histidine hydrochloride. The amounts of L-histidine hydrochloride added and the EPO residual rates after the accelerated testing are shown in Table 4.

TABLE 4

EPO residual rates after accelerated testing of L-histidine hydrochloride-containing preparations

| Amino acid | Amount added (mg/ml) | EPO residual rate after 40° C.-2 week accelerated testing (% of initial content) |
|---|---|---|
| Not added | 0 | 91.5 |
| L-histidine hydrochloride | 0.5 | 95.5 |
| | 1 | 97.3 |
| | 5 | 98.1 |
| | 10 | 99.7 |

Figure 3:
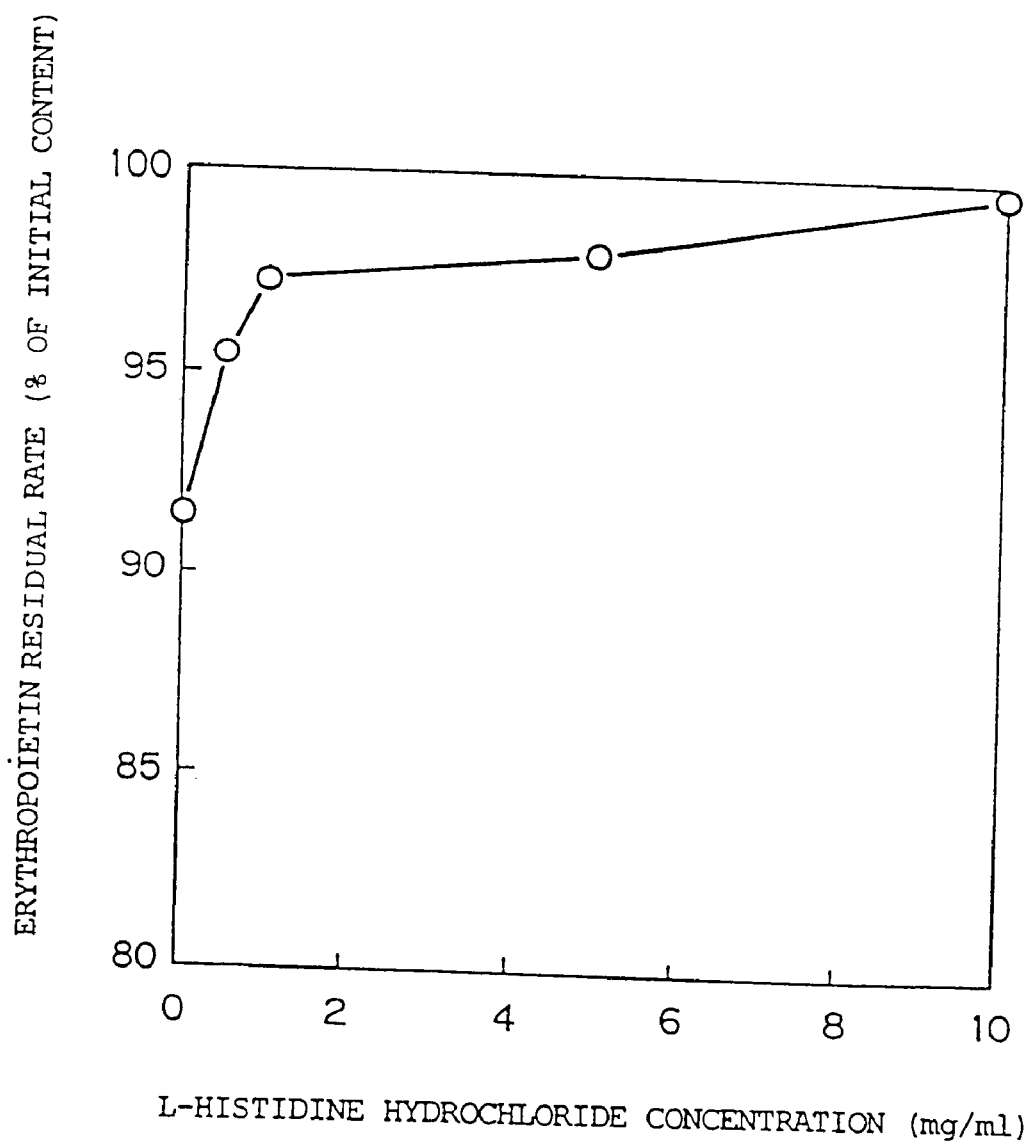
FIG. 3 is a graph showing the relation between the concentration of L-histidine hydrochloride and the residual rate of erythropoietin.

The above results are depicted as a graph in FIG. 3.

As shown above, L-histidine hydrochloride led to maximum EPO residual rates in a concentration range of about 1 to 10 mg/ml.

In accordance with the aforementioned testing method, EPO solution preparations containing L-histidine hydrochloride in various concentrations indicated below were produced, and subjected to a 25° C.-6 month accelerated testing. Then, their EPO residual rates were determined by the RP-HPLC method. The results are shown in Table 5.

TABLE 5

EPO residual rates after accelerated testing of
L-histidine hydrochloride-containing preparations

| Amino acid | Amount added (mg/ml) | EPO residual rate after 25° C.-6 month accelerated testing (% of initial content) |
|---|---|---|
| Not added | 0 | 93.2 |
| L-histidine hydrochloride | 0.5 | 99.3 |
| | 1 | 99.9 |
| | 5 | 97.9 |
| | 10 | 94.1 |

As shown above, L-histidine hydrochloride led to maximum EPO residual rates in a concentration range of 0.5 to 5 mg/ml, especially, at a concentration of 1 mg/ml.

Example 3

Effect of the Addition of Various Amino Acids on EPO Degradation Products

In accordance with the aforementioned testing method, EPO solution preparations containing various amino acids were produced, and subjected to a 40° C.-2 week accelerated testing. Then, the formation of EPO degradation products was investigated by the SDS-polyacrylamide gel electrophoresis analysis method.

1) Preparation of Sample

After the accelerated testing, a 1M TRIS-hydrochloride buffer (pH 6.8) containing SDS, glycerin, and Bromophenol Blue was added to each of the EPO solution preparations containing each of the various amino acids indicated in Table 1 of Example 1. The mixture was heated for 15 minutes at 60° C. for use as a sample solution.

2) Electrophoresis

The sample solution (10 µl) was electrophoresed under the following operating conditions:

a) Equipment: Slab gel electrophoresis apparatus (Bio-Rad Laboratories)
b) Electrophoresis gel:
   SDS-PAGEmini8–16 (concentration gradient gel in polyacrylamide concentrations of 8 to 16%, Tefco)
c) Electrophoresis temperature: 25° C.
d) Electrophoresis conditions:
   25 mA constant current/gel 3) Staining Method (Western Blotting)

The electrophoresed gel was transferred to a polyvinylidene difluoride membrane. Then, anti-EPO rabbit antiserum, biotin-labeled anti-rabbit IgG goat antibody, and biotinylated horseradish peroxidase were used for color development with 3,3'-diaminobenzidine-hydrogen peroxide as a substrate.

4) Results

Figure 4:
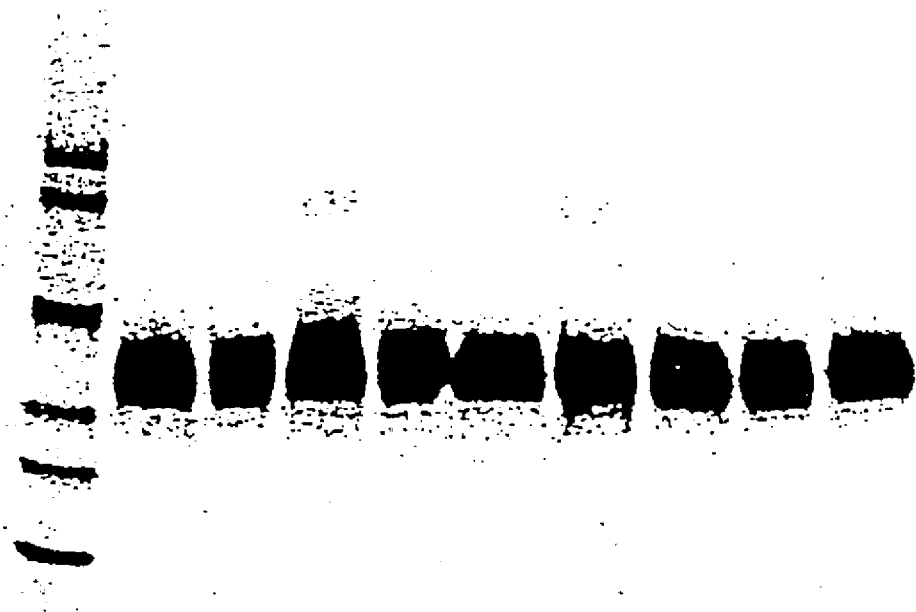
FIG. 4 shows an SDS-polyacrylamide gel electrophoresis pattern illustrating the degradation product suppressing effect of preparations to which various amino acids have been added (an electrophoretogram), in which lane 1: molecular weight marker, lane 2: amino acid-free preparation, lane 3: L-leucine-containing preparation, lane 4: 1-phenylalanine-containing preparation, lane 5: L-tryptophan-containing preparation, lane 6: L-serine-containing preparation, lane 7: L-cysteine-containing preparation, lane 8: monosodium L-glutamate monohydrate-containing preparation, lane 9: L-arginine hydrochloride-containing preparation, and lane 10: L-histidine hydrochloride-containing preparation.

The results obtained are shown in FIG. 4. Compared with the amino acid-free preparation (lane 2), the monosodium L-glutamate monohydrate-containing preparation (lane 8), the L-arginine hydrochloride-containing preparation (lane 9), and the L-histidine hydrochloride-containing preparation (lane 10) showed the marked effect of suppressing the formation of EPO degradation products.

What is claimed is:

1. An erythropoietin solution preparation containing erythropoietin in combination with L-histidine as a stabilizer, wherein the concentration of the L-histidine is 5 mg/ml to 10 mg/ml.

2. The solution preparation of claim 1, which does not contain a protein as a stabilizer.

3. The solution preparation of claim 1 or 2, which further contains a surfactant, a salt, a buffer, or combination thereof.

4. The solution preparation of claim 3, wherein the surfactant is a polyoxyethylene sorbitan alkyl ester.

5. The solution preparation of claim 4, wherein the surfactant is polysorbate 20, polysorbate 80, or combination thereof.

6. The solution preparation of claim 3, wherein the salt is sodium chloride.

7. The solution preparation of claim 3, wherein the buffer is a phosphate buffer, a citrate buffer, or combination thereof.

8. The solution preparation of claim 1 or 2, which does not contain urea.

9. The solution preparation of claim 3, which does not contain urea.

10. A method for stabilizing an erythropoietin solution preparation which comprises adding L-histidine as a stabilizer to the erythropoietin solution preparation, wherein the concentration of L-histidine is 1.0 to 10 mg/ml.

11. A method for stabilizing an erythropoietin solution preparation which comprises adding L-histidine as a stabilizer to the erythropoietin solution preparation, wherein the concentration of L-histidine is 0.5 to 10 mg/ml, and wherein the preparation does not contain L-lysine.

12. The method of claims 10 and 11 further comprising the addition of a surfactant, a salt, a buffer, or combination thereof.

13. The method of claim 12, wherein the surfactant is a polyoxyethylene sorbitan alkyl ester.

14. The method of claim 12, wherein the salt is sodium chloride.

15. The method of claim 12, wherein the buffer is a phosphate buffer, citrate buffer, or combination thereof.

16. A method for stabilizing an erythropoietin solution preparation which comprises adding L-histidine as a stabilizer to the erythropoietin solution preparation, wherein the concentration of L-histidine is 0.5 to 10 mg/ml, and the solution preparation is dissolved in a phosphate buffer, a citrate buffer or combination thereof.

17. The method of claim 6, further comprising the addition of a surfactant, a salt or combination thereof.

18. The method of claim 17, wherein the surfactant is a polyoxyethylene sorbitan alkyl ester.

19. The method of claim 17, wherein the salt is sodium chloride.

* * * * *